United States Patent [19]

Kiozpeoplou

[11] 4,407,788

[45] Oct. 4, 1983

[54] DENTIFRICE

[75] Inventor: Diana Kiozpeoplou, Somerville, N.J.

[73] Assignee: Colgate-Palmolive Company, New York, N.Y.

[21] Appl. No.: 370,660

[22] Filed: Apr. 22, 1982

Related U.S. Application Data

[63] Continuation-in-part of Ser. No. 299,684, Sep. 8, 1981, and Ser. No. 277,774, Jun. 26, 1981, abandoned.

[51] Int. Cl.$^3$ .............................................. A61K 7/16
[52] U.S. Cl. ........................................................ 424/49
[58] Field of Search ................................... 424/49–58

[56] References Cited

U.S. PATENT DOCUMENTS

| | | | |
|---|---|---|---|
| 2,677,700 | 5/1954 | Jackson et al. | 424/49 |
| 2,773,801 | 12/1956 | Fox | 424/57 |
| 2,991,229 | 7/1961 | Ivison | 424/49 |
| 3,020,230 | 2/1962 | Smith | 210/54 |
| 3,906,090 | 9/1975 | Colodney | 424/52 |
| 3,911,104 | 10/1975 | Harrison | 424/52 |
| 3,976,765 | 8/1976 | Nachtigal | 424/54 |
| 4,011,309 | 3/1977 | Lutz | 424/49 |
| 4,036,949 | 7/1977 | Colodney | 424/52 |
| 4,206,198 | 6/1980 | Schmolka | 424/49 |
| 4,259,477 | 3/1981 | Kang | 424/49 |
| 4,323,552 | 4/1982 | Schmolka | 424/49 |
| 4,343,785 | 8/1982 | Schmolka | 424/54 |

FOREIGN PATENT DOCUMENTS

| | | |
|---|---|---|
| 2204670 | 8/1972 | Fed. Rep. of Germany . |
| 51-82739 | 7/1976 | Japan . |
| 53-34934 | 3/1978 | Japan . |
| 55-13251 | 1/1980 | Japan . |
| 1450881 | 3/1974 | United Kingdom . |
| 1425922 | 2/1976 | United Kingdom . |

OTHER PUBLICATIONS

Naganuma et al., Chem. Abstr. 93, #53809x, (1980) of Jpn. Kokai Tokkyo Koho 80 13251, Jan. 30, 1980.
Ozawa et al., Chem. Abstr. 89, #30797v, (1978) of Japan Kokai 78 34934, Mar. 31, 1978.
Lawson et al., Chem. Abstr. 86, #78678x, (1977) of Brit. 1450881, Sep. 29, 1976.
Morton, Chem. Abstr. 85, #25291p, (1976) of Brit. 1425922, Sep. 25, 1976.
Ichikawa et al., Chem. Abstr. 85, #112767s, (1976) of Japan Kokai 76 82739, Jul. 20, 1976.
Clippingdale et al., Chem. Abstr. 77, #130502r, (1972) of Ger. Off. 2204670, Aug. 10, 1972.
Reng. Chem. Abstr. 86, #161019d, (1977) of Parfum. Kosmet. (1976), 57(11): 307–316.
McNeely and Kang Industrial Gums, Ed. R. L. Whistler, Ch. XXI, 2nd Ed., 1973, pp. 473–497.
Mfg. Chem., May 1960: 206–208, Copies in Sn. 299,684.

*Primary Examiner*—Shep K. Rose
*Attorney, Agent, or Firm*—Robert L. Stone; Murray M. Grill; Herbert S. Sylvester

[57] ABSTRACT

A dentifrice containing a siliceous polishing material and binding or gelling agent including resinous poly(ethylene oxide). The polishing agent flocculates in the presence of the resinous poly(ethylene oxide) and provides the dentifrice with desirable stain removal effectiveness without unduly raising dentin abrasion. Foaming character is also achieved when a polyoxyethylene-polyoxypropylene block copolymer and xanthan are present.

6 Claims, No Drawings

DENTIFRICE

This application is a continuation-in-part of U.S. application Ser. No. 299,684, filed Sept. 8, 1981 and U.S. application Ser. No. 277,774 filed June 26, 1981, now abandoned.

This invention relates to a dentifrice which provides effective stain removal.

In ancestor applications, Ser. Nos. 277,774 and 299,684, dentifrices are described which provide excellent foaming with the use of the nonionic surface active agent block copolymer of polyoxyethylene-polyoxypropylene with xanthan as gelling or binding agent in which resinous poly(ethylene oxide) may also be present. The dentifrice thereof typically contains a dentally acceptable polishing agent such as a siliceous material; for instance, colloidal silica or synthetic alkali metal aluminosilicate complex, that is, material in which silica contains combined alumina.

Based upon prior art considerations, as disclosed in U.S. Pat. No. 3,020,230 to Smith, wherein silica material is stated to coagulate or flocculate in the presence of resinous poly(ethylene oxide) in order to precipitate it from a liquid suspension, one skilled in the dentifrice art would not have been led to use silica materials in a dentifrice containing resinous poly(ethylene oxide). Indeed, in U.S. Pat. No. 2,991,229 to Ivison, polishing agents or abrasives disclosed in a toothpaste containing poly(ethylene oxide) were "tricalcium phosphate, dicalcium phosphate and calcium carbonate and the like;" but not silica materials.

It is an advantage of the present invention that a dentifrice is provided with improved stain removal which has acceptable cosmetic rheology and dentin abrasion characteristics.

It is a further advantage that desirable foaming is achieved with inclusion of polyoxyethylene-poly oxypropylene block copolymer and xanthan in the dentifrice.

Further advantages will be apparent from consideration of the following disclosure.

In accordance with certain of its aspects, this invention relates to a dentifrice comprising about 20–80% by weight of a liquid humectant vehicle, about 5–50% by weight of a siliceous polishing material and about 0.05–5% by weight of a resinous poly(ethylene oxide), said dentifrice containing flocculated particles of said siliceous polishing agent in the presence of said poly(ethylene oxide).

The proportion of the siliceous polishing agent content is in the range from 5% to 50% by weight of the dentifrice, preferably from 10% to 30% such as from 10% to 25%. One such polishing agent is a complex alkali metal aluminosilicate having a refractive index of from 1.44 to 1.47 and containing at least 70% silica, up to 10% alumina, such as about 0.1–10% e.g. about 0.1–3%, preferably up to about 20% of moisture, such as about 0.5–10%; and up to about 10% of alkali metal oxide. Typically, this material has a particle size in the range from 1 to 35 microns, preferably from 2 to 20 microns, e.g. 2 to 4 microns. The preferred moisture content is from 10% to 20% measured by ignition at 1000° C. and the typical content of alkali metal oxide is from 5% to 10%. Generally, the polishing agent has a loose bulk density of up to 0.2 g/cc, such as from 0.07 to 0.12 g/cc. Another suitable type of polishing agent is porous amorphous silicic anhydride having an average particle size preferably below 20 microns and above 1 micron, a surface area of at least 200 m$^2$/g, preferably at least 300 m$^2$/g, and a bulk density of at least 0.15 g/cm$^3$, preferably at least 0.30 g/cm$^3$, such as a dehydrated silica hydrogel (i.e. a xerogel), preferably of the well known regular density or intermediate density type. Examples of such amorphous silicic anhydride polishing agents are "Syloid 63", "Syloid 72", and "Syloid 74" (SYLOID is a trade mark) which are described in "The Davison Family of Syloid Silicas" published by their manufacturer, Grace, Davison Chemical Company. "Santocel 100" of Monsanto (SANTOCEL is a trade mark), is also a suitable dental abrasive. "Syloid 72" has an average particle size of about 4 microns, a surface area of about 340 m$^2$/g bulk density of about 1.77 g/cm$^3$. For "Syloid 63" the corresponding figures are about 9 microns, about 675 m$^2$/g and about 0.4 g/cm$^3$. A grade of "Santocel 100" has a surface area of about 239 m$^2$/g and a bulk density of about 0.24 g/cm$^3$. These amorphous silicic anhydrides may be used singly or in mixtures.

Resinous poly(ethylene oxide) has been disclosed as a dentifrice gelling or binding agent in U.S. Pat. No. 2,991,229 to Ivison. Its presence smoothed the texture of the dentifrice; indeed, the dentrifrice of the present invention has a smooth texture even though flocculated particles from the siliceous polishing material are present.

The poly(ethylene oxides) employed in this invention are solid, colorless, water-soluble resins. They appear to form homogeneous systems in water in all proportions, although the relatively higher molecular weight ethylene oxide polymers merely swell on the addition of small amounts of water. On the addition of greater amounts of water, the polymers pass into solution. The water solutions are viscous, the viscosity increasing both with the concentration of the polymer in the solution and the reduced viscosity of the polymer. The ethylene oxide polymers employed in this invention show little change in melting point with reduced viscosity (an indication of increased molecular weight) and the melting point, as measured by change in stiffness with temperature, was found to be about 65°±2° C. throughout the range of reduced viscosities of from about 1.0 to about 10, and greater. These polymers, upon X-ray examination, disclose a crystalline structure similar to that exhibited by polyethylene. The crystallization temperature, as determined from measuring the break in the cooling curve, is about 55° C. To facilitate the understanding of the instant invention, various terms will be defined. At the outset it should be noted that the word "poly(ethylene oxide)" as used throughout the specification and claims refers to ethylene oxide polymers which have a reduced viscosity in acetonitrile of at least 0.5 and upwards to 75, and higher.

Unless otherwise stated, by the term "reduced viscosity," as used herein, is meant a value obtained by dividing the specific viscosity of the concentration of the ethylene oxide polymer in the solution, the concentration being measured in grams of polymer per 100 milliliters of solvent at a given temperature, and is regarded as a measure of molecular weight. The specific viscosity is obtained by dividing the difference between the viscosity of the solution and the viscosity of the solvent by the viscosity of the solvent. The reduced viscosities herein referred to are measured at a concentration of 0.2 grams of poly(ethylene oxide) in 100 milliliters of acetonitrile at 30° C. (unless stated otherwise).

Granular poly(ethylene oxide) results from the suspension polymerization of an agitated reaction mixture comprising ethylene oxide in contact with a polymerization catalyst therefor and in the presence of an inert organic diluent, e.g., heptane, in which ethylene oxide is soluble and the resulting poly(ethylene oxide) is insoluble. Granular poly(ethylene oxide) thus produced is obtained in a finely-divided solid particle state and resembles finely-divided sand in particle size. Unlike the granular poly(ethylene oxide) resulting from the suspension polymerization process, the bulk and solution polymerization processes yield a polymer which is a substantially homogeneous mass either conforming to the shape of the reaction vessel or, after driving off the organic medium, for example, by mechanical extrusion, e.g. Marshall Mill (under vaccum and at slightly elevated temperatures), resembles layers or sheets. This polymer subsequently can be reduced in particle size, for example, by dicing or the like.

The term "granular" refers to the particle size of the ethylene oxide polymers prepared by suspension polymerization. A granular product is one which is in a free-flowing state and comprises particles averaging less than 5 mesh in size (U.S. Standard Size Sieve).

The poly(ethylene oxide) comprises about 0.05-5% by weight of the dentifrice, preferably about 0.1-1.5%.

In the dentifrice, the siliceous polishing agent flocculates in situ in the presence of the poly(ethylene oxide). The flocculated particles typically may agglomerate with each other and have apparent particle sizes up to about 250 microns or more, typically about 44 to 177 microns; in other words, the flocculated particles typically pass through a screen of U.S. Sieve No. 80 and are retained on a screen on U.S. Sieve No. 325.

In spite of the presence of the flocculated particles the dentifrice is readily formulated to have a desirable appearance and a rheological texture without an undue "lumpy" appearance or "gritty" feel.

The liquid vehicle of the dentifrice comprises water, humectant or mixtures thereof in amount of about 20–80%, preferably about 30–60%. When a substantially visually clear gel is desired, water is generally not present in amount above about 10% typically about 2-5%. When the dentifrice is opacified, greater amounts of water may be present. Typical humectants include sorbitol (as 70% aqueous solution), glycerine, maltitol, xylitol, polyethylene glycol 400 and polyethylene glycol 600. Most preferably the dentifrice contains about 25-50% maltitol. Maltitol may assist in improving stain removal when present in the dentifrice of the invention. It is noted that maltitol is disclosed as a dentifrice ingredient in Japanese Patent Publications 73/10241 and 65/15120.

The liquid vehicle and gelling agent including resinous poly(ethylene oxide) and other components of the dentifrice are proportioned to form a cream or gel mass of desired consistency which is extrudible from an aerosol or pump container or a collapsible tube (for example aluminum, lead or plastic).

In addition to the resinous poly(ethylene oxide), further gelling or binding agent such as sodium carboxymethyl cellulose, Irish moss, xanthan and the like may be present in amount of about 0.5–7%. Xanthan is preferred. The total amount of gelling or binding agent in the dentifrice can be about 0.1–12% by weight.

Xanthan gum is a fermentation product prepared by action of the bacteria of the genus Xanthomonas upon carbohydrates. Four species of Xanthomonas, viz. X. campetris. X. phaseoli, X. malvocearum, and X. carotae are reported in the literature to be the most efficient gum producers. Although the exact chemical structure is not determined, it is generally accepted to be a heteropolysaccharide with a molecular weight of several million. It contains D-glucose, D-mannose and D-glucoronic acid in molar ratio of 2.8:3:2.0. The molecule contains 4.7% acetyl and about 3% pyruvate. The proposed chemical structure configuration can be found in McNeely and Kang, Industrial Gums, Ed. R. L. Whistler, Ch XXI, 2nd Edition, New York, 1973. The procedure for growing, isolating and purifying the xanthan gum is found in Manufacturing Chemist, May 1960, pages 206–208 (including mention at page 208 of potential use of gums therein described for formulating toothpastes).

Use of special grades of xanthan gum, such as described in U.S. Pat. No. 4,263,399 are within the scope of this invention. A grade described in U.S. Pat. No. 4,263,399 is a xanthan gum in which up to about 1.6% of the carboxyl groups are bound to calcium and the remaining carboxyl groups are bound to sodium, potassium, a mixture of sodium and potassium or other non-calcium cations.

The dentifrice may contain an anionic, nonionic, cationic or amphoteric surface active agent to achieve increased prophylactic action, assist in achieving thorough and complete dispersion of the instant compositions in the oral cavity and render the instant compositions more cosmetically acceptable.

A preferred surface active agent is a nonionic block copolymer containing polyoxyethylene and polyoxypropylene. Such block copolymers are available from Wyandotte Chemicals Corp. under the trade mark "Pluronic". They may be liquid, paste, or solid and are generally chemically defined in terms of the molecular weight of the polyoxypropylene hydrophobic moiety and the percent by weight of the polyoxyethylene hydrophilic moiety.

The following block copolymers are available from Wyandotte:

| PLURONIC NUMBER | | PHYSICAL CHARACTER | HYDRO-PHIL | MOL. WT. HYDROPROBE |
|---|---|---|---|---|
| L | 121 | LIQUID | 10 | 4000 |
| L | 101 | LIQUID | 10 | 3250 |
| L | 81 | LIQUID | 10 | 2250 |
| L | 61 | LIQUID | 10 | 1750 |
| L | 31 | LIQUID | 10 | 950 |
| L | 122 | LIQUID | 20 | 4000 |
| L | 92 | LIQUID | 20 | 2750 |
| L | 72 | LIQUID | 20 | 2050 |
| L | 52 | LIQUID | 20 | 1750 |
| L | 42 | LIQUID | 20 | 1200 |
| P | 123 | PASTE | 30 | 4000 |
| P | 103 | PASTE | 30 | 3250 |
| L | 63 | LIQUID | 30 | 1750 |
| L | 43 | LIQUID | 30 | 1200 |
| P | 104 | PASTE | 40 | 3250 |
| P | 94 | PASTE | 40 | 2750 |
| P | 84 | PASTE | 40 | 2250 |
| L | 64 | LIQUID | 40 | 1750 |
| L | 44 | LIQUID | 40 | 1200 |
| P | 105 | PASTE | 50 | 3250 |
| P | 85 | PASTE | 50 | 2250 |
| P | 75 | PASTE | 50 | 2050 |
| P | 65 | PASTE | 50 | 1750 |
| L | 35 | LIQUID | 50 | 950 |
| F | 127 | SOLID | 70 | 4000 |
| F | 87 | SOLID | 70 | 2250 |
| F | 77 | SOLID | 70 | 2050 |
| F | 108 | SOLID | 80 | 3250 |

| PLURONIC NUMBER | PHYSICAL CHARACTER | HYDRO-PHIL | MOL. WT. HYDROPROBE |
|---|---|---|---|
| F 98 | SOLID | 80 | 2750 |
| F 88 | SOLID | 80 | 2250 |
| F 68 | SOLID | 80 | 1750 |
| F 38 | SOLID | 80 | 950 |

The preferred nonionic block copolymers are solid (or flake) materials and the most preferred are Pluronic 108 (80% polyoxyethylene: 3250 molecular weight polyoxypropylene) and F 87 (70% polyoxyethylene: 2250 molecular weight polyoxypropylene).

Other nonionic surface active agents which may be employed include condensates of sorbitan monosterate with approximately 20 moles of ethylene oxide. Amphoteric agents include quaternized imidazole derivatives which are available under the trademark "Miranol" such as Miranol $C_2M$. Suitable types of anionic detergents are water-soluble salts of higher fatty acid monoglyceride monosulphates, such as the sodium salt of the monosulphated monoglyceride of hydrogenated coconut oil fatty acids, higher alkyll sulphates, such as sodium lauryl sulphate, alkyl aryl sulphonates, such as sodium dodecyl benzene sulphonate, olefin sulphonates, such as sodium olefin sulphonate in which the olefin group contains 12-21 carbon atoms, higher alkyl sulphoacetates, higher fatty acid ester of 1,2-dihydroxy propane sulphonates, and the substantially saturated higher aliphatic acyl amides of lower aliphatic amino carboxylic acid compounds, such as those having 12-16 carbons in the fatty acid, alkyl or acyl radicals, and the like. Examples of the last mentioned amides are N-lauroyl sarcosine and the sodium, potassium, and ethanolamine salts of N-lauroyl, N-myristoyl or N-palmitoyl sarcosine, which could be substantially free from soap or similar higher fatty acid material which tends to substantially reduce the effect of these compounds. The use of these sarcosine compounds in dentifrice compositions of the present invention is particularly advantageous since these materials exhibit a prolonged and marked effect in the inhibition of acid formation in the oral cavity due to carbohydrates breakdown in adition to exerting some reduction in the solubility of tooth enamel in acid solution.

Cationic surface active germicides and antibacterial compounds such as di-isobutylphenoxyethoxyethyl dimethyl benzyl ammonium chloride, benzyl dimethyl stearyl ammonium chloride, tertiary amines having one fatty alkyl group (of from 12-18 carbon atoms) and two (poly)oxyethylene groups attached to the nitrogen (typically containing a total of from about 2 to 50 ethanoxy groups per molecule) and salts thereof with acids, and compounds of the structure.

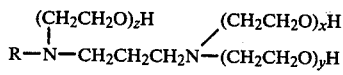

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the instant dentifrice.

An alkali metal fluorine-providing compound may be employed in the dentifrice of the invention. The alkali metal fluorine-providing compound includes sodium fluoride, potassium, fluoride, lithium fluoride, ammonium fluoride and complex fluorides, particularly alkali metal monofluorophosphates. These compounds exhibit satisfactory retentions of soluble fluoride in dentifrices of the instant invention. In particular, the level of retention of monofluorophosphate ion as fluoride with the alkali metal monofluorophosphates is quite high. The fluorine-containing compound is employed in amount which provides an effective nontoxic amount of fluorine-containing ion to the dentifrice typically about 0.01-1% by weight preferably about 0.1% fluorine. Thus, sodium fluoride is typically employed in amount of about 0.02-2% by weight, preferably about 0.2%, and sodium monofluorophosphate, $Na_2PO_3F$, in amount of about 0.1-7.6% by weight, preferably about 0.76%.

The alkali metal monofluorophosphates which may be employed include sodium monofluorophosphate, lithium monofluorophosphate, potassium monofluorophosphate and ammonium monofluorophosphate. The preferred salt is sodium monofluorophosphate, $Na_2PO_3F$, which as commercially available, may vary considerably in purity. It may be used in any suitable purity provided that any impurities do not substantially adversely affect the desired properties. In general, the purity is desirably at least about 80%. For best results, it should be at least 85%, and preferably at least 90% by weight of sodium monofluorophosphate with the balance being primarily impurities or by-products of manufacture such as sodium fluoride, water-soluble sodium phosphate salt, and the like. Expressed in another way, the sodium monofluorophosphate employed should have a total fluoride content of above 12%, preferably 12.7%; a content of not more than 1.5%, preferably not more than 1.2% of free sodium fluoride; and a sodium monofluorophosphate content of at least 12%, preferably at least 12.1%, all calculated as fluoride.

Other monofluorophosphate salts which may be used in the instant invention include monofluoropolyphosphates such as $Na_4P_3O_9F$, $K_4P_3O_9F$, $(NH_4)_4P_3O_9F$, $Na_3KP_3O_9F$, $(NH_4)_3NaP_3O_9F$ and $Li_4P_3O_9F$.

Antibacterial agents may also be employed in the oral preparations of the instant invention to provide a total content of such agents of up to about 5% by weight. Typical antibacterial agents include:

$N^1$-(4-chlorobenzyl)-$N^5$-(2,4-dichlorobenzyl) biguanide;
p-chlorophenyl biguanide;
4-chlorobenzyhydryl biguanide;
4-chlorobenzyhydrylguanylurea;
N-3-lauroxypropyl-$N^5$-p-chlorobenzylbiguanide;
1-(lauryldimethylammonium)-8-(p-chlorobenzyl-dimethylammonium) octane dichloride;
5,6-dichloro-2-guanidinobenzimidazole;
$N^1$-p-chlorophenyl biguanidohexane;
1,6-bis(2-ethylhexyl biguanido) hexane;
5-amino-1,3- bis(2-ethylhexyl)-5-methylhexahydropyrimidine;
and their non-toxic acid addition salts.

Synthetic finely divided pyrogenic silica such as those sold under the trademarks Cab-O-Sil M-5, Syloid 244, Syloid 266 and Aerosil D-200 may also be employed in amounts of about 1-5% by weight to promote thickening or gelling of the dentifrice.

The taste of the new composition may be modified by employing suitable flavoring or sweetening materials. Examples of suitable flavoring constituents include the flavoring oils, e.g. oils of spearmint, peppermint, wintergreen, sassafras, clove, sage, eucalyptus, marjoram, cinnamon, lemon and orange as well as methylsalicylate. Suitable sweetening agents include sucrose, lactose, maltose, sorbitol, sodium cyclamate, perillartine, and saccharine. Suitable flavor agent may comprise from about 0.01 to 5% or more of the compositions particularly when anionic surface active agent is present in the instant invention.

Various other materials may be incorporated in the dentifrice formulations of this invention. Examples thereof are coloring or whitening agents or dyestuffs, preservatives, silicones, chlorophyll compounds, ammoniated materials such as urea, diammoniumphosphate and mixtures thereof, and other constituents. These adjuvants are incorporated in the instant compositions in amounts which do not substantially adversely effect the properties and characteristics are desired and selected and used in proper amount depending upon the particular type of preparation involved.

The dentifrices should have a pH practicable for use. A moderately acid to alkaline pH is preferred.

The following specific examples are further illustrative of the nature of the present invention but is understood that the invention is not limited thereto. Dentifrice formulations are prepared in the usual manner and provide in situ flocculation of the siliceous polishing material, and all amounts and proportions are by weight except as otherwise indicated.

EXAMPLE 1

The following opacified gel dentifrices are prepared:

|  | PARTS | |
| --- | --- | --- |
|  | A | B |
| Maltitol (75% solution) | 40.00 | 40.00 |
| Sodium aluminosilicate (silica containing about 1% combined alumina - Zeo 49B-Huber) | 18.00 | 18.00 |
| Pluronic F 108 Block Copolymer | 3.00 | 3.00 |
| Xanthan | 1.70 | 1.70 |
| Polyox WSR 301 (Union Carbide) | 0.20 | — |
| Titanium dioxide | 0.40 | 0.40 |
| Flavor | 0.50 | 0.50 |
| Sodium saccharin | 0.20 | 0.20 |
| Deionized water | Q.S. TO 100 | Q.S. TO 100 |

Polyox WSR-301 is available from Union Carbide Corp. as granules of water soluble poly (ethylene oxide) resin having a molecular weight of about 4,000,000 and a Brookfield viscosity of 1650–3850 cps. (25° C., spindle 1, speed 2 rpm) when in water at 1% by weight. Likewise, similar foam and feel is attained when other water-soluble poly (ethylene oxide) resins available from Union Carbide Corp. as Polyox WSR-N-10, WSR-N-80, WSR-N-750, WSR-N-3000, WSR-205 and WSR 1105 replace Polyox WSR-301, in different concentrations.

Both dentifrices provide stable full-bodied foam with good mouth feel; the mouth feel of dentifrice A being particularly satisfactory.

When compared for ability to remove dental stain and in dentin abrasion, dentifrice A containing the Polyox material removes more stain with less dentin abrasion than dentifrice B, without Polyox material. In dentifrice A, flocculated particles of sodium aluminosilicate form in situ.

The results are as follows:

| DENTIFRICE | PERCENT STAIN REMOVAL | RADIOACTIVE DENTIN ABRASION |
| --- | --- | --- |
| A | 35 | 14 |
| B | 22 | 39 |

In a stain removal test, sections of human dental enamel are etched with 0.1 N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical brushing machine for 500 reciprocal strokes with a slurry of a dentifrice and the residual stain measured with the meter. Finally, the stain which remains is completely removed with dental pumice and the reflectance of this surface is read. The ability of a dentifrice to remove the stain is expressed by the following equation.

$$\text{Percent stain removed} = \frac{(Rd_{500\text{ strokes}} - Rd_{\text{initial}}) \cdot 100}{Rd_{\text{pumiced}} - Rd_{\text{initial}}}$$

where $Rd_{\text{initial}}$, $Rd_{500\text{ strokes}}$, and $Rd_{\text{pumiced}}$ are respectively the reflectance values measured on the initially stained surfaces, after brushing for 500 reciprocal strokes and after removing the residual stain by pumicing.

The RDA values are obtained by a procedure based on a radioactive technique described in the literature; Stookey, C. K. and Muhler, J. C., J. Dental Research 47 524–538 (1968); Hefferren, J. J., J. Dental Research 55 563–573 (1976).

EXAMPLE 2

The following dentifrices are prepared:

|  | PARTS | |
| --- | --- | --- |
|  | A | B |
| Maltitol (75% solution) | 40.00 | 40.00 |
| Sodium aluminosilicate (silica containing combined about 1% combined alumina - Zeo 49B - Huber) | 18.00 | 18.00 |
| Calcined alumina | 5.00 | 5.00 |
| Pluronic F-108 | 3.00 | 3.00 |
| Xanthan | 1.70 | 1.70 |
| Polyox WSR 301 (Union Carbide) | 0.20 | — |
| Titanium dioxide | 0.40 | 0.40 |
| Flavor | 0.50 | 0.50 |
| Sodium saccharin | 0.10 | 0.10 |
| Deionized water | Q.S. to 100 | Q.S. to 100 |

Both dentifrices provide stable full-bodied foam with good mouth feel; the mouth feel of dentifrice A being particularly satisfactory.

The following stain removal and radioactive dentin abrasion results were obtained with dentifrices A and B, evidencing superiority for dentifrice A, containing the Polyox material with regard to higher stain removal with similar dentin abrasion.

| DENTIFRICE | PERCENT STAIN REMOVAL | RDA |
| --- | --- | --- |
| A | 65 | 44 |

-continued

| DENTIFRICE | PERCENT STAIN REMOVAL | RDA |
| --- | --- | --- |
| B | 47 | 41 |

EXAMPLES 3-4

The following opacified gel dentifrices are prepared:

|  | EXAMPLES | |
| --- | --- | --- |
|  | 3 | 4 |
| Glycerine | 10.0 | 10.0 |
| Maltitol | 15.0 | 15.0 |
| Sodium aluminosilicate (silica combined with about 1% combined alumina) Zeo 49B (Huber) | 18.0 | 18.0 |
| Pluronic 108 block copolymer | — | 3.0 |
| Sodium lauryl sulfate | 1.0 | — |
| Xanthan | 2.0 | 2.0 |
| Polyox WSR 301 | 0.2 | 0.2 |
| Sodium monofluorophosphate | 0.76 | 0.76 |
| Titanium dioxide | 0.4 | 0.4 |
| Low menthol flavor | — | 0.5 |
| Peppermint oil flavor | 0.5 | — |
| Sodium saccharin | 0.2 | — |
| Color solution (1%) | 0.05 | 0.05 |
| Water | Q.S. to 100 | Q.S. to 100 |

The dentifrice of Example 3 with sodium lauryl sulfate has desirable foam character. The dentifrice of Example 4 also has very good stable full-bodied foam character even though no anionic surface active agent is employed. The foam remains throughout the oral cavity, with desirable mouth feel, when the dentifrice is brushed onto the teeth. Moreover, it has no bitter note even though low menthol flavor is present and no sweetener is added. The dentifrices have fine smooth texture and appearance, effectively remove stain and have acceptable dentin abrasion character. They contain flocculated particles of sodium aluminosilicate.

Although this invention has been described with regard to illustrative examples, it will be apparent to one skilled in the art that various modifications may be made thereto which fall within its scope.

I claim:

1. A dentifrice which reduces dental stain comprising about 20-80% by weight of a liquid humectant vehicle, about 5-50% by weight of a siliceous polishing material and about 0.05-5% by weight of a resinous poly(ethylene oxide), said dentifrice containing flocculated particles formed by said siliceous polishing material in the presence of said poly(ethylene oxide).

2. The dentifrice claimed in claim 1 wherein said resinous poly(ethylene oxide) has a reduced viscosity of at least 0.5 as measured at a concentration of 0.2 gram of said poly(ethylene oxide) in 100 milliliters of acetonitrile at 30° C.

3. The dentifrice claimed in claim 2 wherein said resinous poly(ethylene oxide) is present in amount of about 0.1-1.5% by weight.

4. The dentifrice claimed in claim 1 wherein said siliceous polishing material is a complex alkali metal aluminosilicate having a refractive index of from 1.44 to 1.47.

5. The dentifrice claimed in claim 4 wherein said alkali metal aluminosilicate is sodium aluminosilicate wherein silica is combined with about 0.1-3% alumina.

6. The dentifrice claimed in claim 1 wherein said flocculated particles have an apparent particle size of about 44 to 177 microns.

* * * * *